(12) United States Patent
Nolan

(10) Patent No.: US 6,540,990 B2
(45) Date of Patent: Apr. 1, 2003

(54) PHYSIOLOGICAL METHOD OF IMPROVING VISION

(76) Inventor: Gerard M. Nolan, P.O. Box 827, Ave., Farmington, CT (US) 06032

(*) Notice: Subject to any disclaimer, the term of this patent is extended or adjusted under 35 U.S.C. 154(b) by 0 days.

(21) Appl. No.: 09/929,152

(22) Filed: Aug. 13, 2001

(65) Prior Publication Data

US 2003/0036535 A1 Feb. 20, 2003

Related U.S. Application Data

(63) Continuation of application No. 09/773,878, filed on Jan. 31, 2001, and a continuation of application No. 09/667,270, filed on Sep. 22, 2000, now Pat. No. 6,273,092.

(51) Int. Cl.⁷ ............................................. A61K 31/74
(52) U.S. Cl. ................................. 424/78.04; 514/912
(58) Field of Search ...................... 424/78.04; 514/912

(56) References Cited

U.S. PATENT DOCUMENTS

| | | | | |
|---|---|---|---|---|
| 4,490,379 A | * | 12/1984 | Podos et al. | 424/262 |
| 4,977,176 A | * | 12/1990 | Amstulz et al. | 514/397 |
| 5,288,735 A | | 2/1994 | Trager et al. | 514/363 |
| 6,273,092 B1 | | 8/2001 | Nolan | 128/898 |

OTHER PUBLICATIONS

Physician's Desk Reference; 2001, 29th edition; pp. 321–323.
Adams, Chromatic and Luminosity Processing in Retinal Disease, American Journal of Optometry & Physiological Optics; Dec. 1982; vol. 59 (12): 954–960.
Bowman, The Clinical Assessment of Colour Discrimination in Senile Macular Degeneration, Acta Ophthalmologica, 1980 vol. 58 (3): 337–346.
Bowman, The Relationship Between Color Discrimination and Visual Acuity in Senile Macular Degeneration, American Journal of Optometry, Mar. 1980; vol. 57 (3): 145–148.
Bresnick et al., Autosomal Dominantly Inherited Macular Dystrophy with Preferential Short-Wavelength Sensitive Cone Involvement, American Journal of Ophthalmology, Sep. 15, 1989; 108: 265–276.
Cheng et al., Visual Losses in Early Age-Related Maculopathy, Optometry and Vision Science, Feb. 1993; vol. 70 (2): 89–96.
Chu, et al., Clinical Studies of Color Vision with Gunkel's Chromagraph, Arch Ophthalmol Aug. 1983; vol. 101: 1232–1235.
Fishman, et. al., Color Vision Defects in Retinitis Pigmentosa, Annals of Ophthalmology, May 1981; 13 (5): 609–618.
Zrenner, et. al., Cone Function and Cone Interaction in Hereditary Degenerations of the Central Retina, Documents Ophthalmologica, Jan. 31, 1986; vol. 62 (1): 5–12.
Holz, et. al., Colour Contrast Sensitivity in Patients with Age-Related Bruch's Membrane Changes, German J. Ophthalmol Nov. 1995; vol. 4 : 336–341.
Kellner, et. al.; Hereditary Macular Dystrophies, Ophthalmologe 1998, Sep. 95; vol. 9: 597–601 (Summary in English).
Mantyjarvi et al., Color Vision in Stargardt's Disease, International Ophthalmology Nov. 1992; 16 (6): 423–428.
Minato, Color Vision Defects of Macular Diseases; Nippon Ganka Gakkai Zasshi; ACTA Soc. Ophthalmol Japan; Apr. 1991; vol. 95: 354–362 (Abstract in English).
Smith, et. al., Color Matching and the Stiles-Crawford Effect in Observers with Early Age-Related Macular Changes, J Opt Soc Am A Dec. 1988; vol. 5 (12): 2113–2121.
Swanson, et. al., Color Matches in Diseased Eyes with Good Acuity: Detection of Deficits in Cone Optical Density and in Chromatic Discrimination, J Opt Soc Am A Oct. 1995; vol. 12 (10); 2230–2236.

* cited by examiner

Primary Examiner—Zohreh Fay
(74) Attorney, Agent, or Firm—William J. McNichol, Jr.; Nanda P. B. A. Kumar; ReedSmith LLP

(57) ABSTRACT

The present invention is directed to a physiological method for improving vision in a human patient. This method involves topical application to the eye, an amount of acetylcholine esterase inhibitor containing composition so that it is sufficient to provide a therapeutic benefit to improve the visual acuity in the human patient. The composition is administered topically and at bedtime after an eye straining work for about 20 minutes. The method disclosed herein is used for treatment and prevention of congenital and acquired color vision blindness, treatment of ocular hypertension and glaucoma, prevention of the progression of myopia, treatment of strabismus or squint, potentiation of best visual acuity, neuro-protection, treatment of aberrations secondary to pupil dilation.

44 Claims, No Drawings

PHYSIOLOGICAL METHOD OF IMPROVING VISION

This application claims the benefit of the continuation of U.S. application Ser. No. 09/667,270 filed Sep. 22, 2000 now U.S. Pat. No. 6,273,092, and U.S. application Ser. No. 09/773,878 filed Jan. 31, 2001 which applications are incorporated herein by reference.

FIELD OF THE INVENTION

The present invention relates to a newly identified pharmacological treatment to treat age related diseases or disorders of the both the anterior and posterior segment of the eye or to potentiate best visual acuity. Specifically, the invention provides methods for treatment and prevention of congenital and acquired color vision blindness, treatment of ocular hypertension and glaucoma, prevention of the progression of myopia, treatment of strabismus or squint, potentiation of best visual acuity, neuro-protection, treatment of aberrations secondary to pupil dilation by topical administration of acetylcholine esterase inhibitors.

BACKGROUND OF THE INVENTION

The image of an infinite distant object will fall in front of the retina in myopia (nearsightedness) on the retina in emmetropia (normal sightedness) and behind the retina in hyperopia (farsightedness), when these eyes are exerting zero accommodation. The emmetropic eye forms sharp retinal imagers of distant objects with the lens of the eye in relaxed accommodation. This ideal optical human condition of emmetropia is possible as a result of a function of corneal curvature and axial length of the eye and takes into account that parallel rays of light travel from air will bend when passing through the cornea surface and into the liquid environment of the eye. Normally, the emmetrope can see distant scenes sharply and, in addition, can see objects held close to the eye without awareness of any focusing by the eye. The process of focusing upon a near object, called accommodation, is accomplished by the muscles of the ciliary body of the eye contracting to vary the shape of the crystalline lens of the eye. To see at a distance, the ciliary muscles are relaxed; to see nearby, the ciliary body contracts to reshape the lens. The amount of accommodation exerted from the relaxed state of the muscles of the ciliary body to the contracted state of the ciliary muscles (i.e., to full accommodation) of the eye is termed the amplitude of accommodation. When the eye is fully accommodated, the point in space which is focused upon the retina is called the near point of the eye, or the nearest point of distinct vision.

Accommodation is measured in diopters. A diopter is defined as 1/the distance in meters to the near point of vision. In both emmetropic individuals and myopic individuals, who have been treated by corneal surgery, the ability to accommodate is gradually lost with age. In fact, the ability to reshape the lens to focus upon a near point may be completely lost after age 40 years. This decrease in the amplitude of accommodation and the consequent loss of near vision is called presbyopia and is thought to be a normal part of the aging process. The inverse relationship between age and the amplitude of accommodation can be seen in Table 1.

TABLE 1

Relationship Between Age, Amplitude of Accommodation and Near Vision for Emmetrope

| Age | Amplitude of Accommodation (Diopters) | Near Point For Emmetrope (cm) |
|-----|---------------------------------------|-------------------------------|
| 10  | 14.0                                  | 7.0                           |
| 20  | 10.0                                  | 10.0                          |
| 30  | 7.0                                   | 14.2                          |
| 40  | 4.5                                   | 22.2                          |
| 45  | 3.5                                   | 28.5                          |
| 50  | 2.5                                   | 40.0                          |
| 55  | 1.75                                  | 57.0                          |
| 60  | 1.00                                  | 100.0                         |
| 65  | 0.50                                  | 200.0                         |
| 70  | 0.25                                  | 400.00                        |

Physiologically, accommodation is under the influence of the parasympathetic nervous system and occurs through the chemical action of acetycholine on muscle fibers of the ciliary body. Contraction of the ciliary body muscles decreases the tension of the lens ligaments, which allows the lens to focus at near point.

Acetylcholine, when working on the eye or other smooth muscles of the body is regulated by cholinesterase enzyme which breaks down acetylcholine and thus turns off its parasympathetic effect on muscles. In an effort to correct presbyopia, the effect of acetylcholine on the muscles of the eye could be increased either by adding an acetylcholine like drug such as pilocarpine, or by blocking the breakdown of acetylcholine with a drug which inhibits the natural cholinesterase (e.g., a cholinesterase inhibitor).

There have been problems with the first approach; When pilocarpine hydrochloride, an acetylcholine like drug, sold as SALAGER® (MGI Pharma, Minnetonka, Minn.), is applied to an emmetropic eye, the increased parasympathetic effect leads to enhanced near vision but at the sacrifice of distant vision. The emmetropic eye becomes myopic as a consequence of this adverse side effect acetylcholine treatment to correct presbyopia has not been effective. Likewise, the second approach, the use of cholinesterase inhibitors, has been unsuccessful because of similar side effects from the cholinesterase drugs used in current concentrations. No other pharmacological agents have been found to restore near vision in an individual with presbyopia. Thus presbyopia is considered untreatable with current pharmacological agents.

A diminished visual acuity or total loss of vision may result from a number of eye diseases or disorders caused by dysfunction of tissues or structures in the anterior region of the eye and/or posterior region of the eye. The eye is divided anatomically into an anterior and posterior segment. The anterior segment includes the cornea, anterior chamber, iris and ciliary body (anterior choroid), posterior chamber and crystalline lens. The posterior segment includes the retina with optic nerve, choroid (posterior choroid) and vitreous. Some of the examples of eye disorders resulting from the pathologic conditions of structures in the anterior segment of the eye are dry eye syndrome, keratitis or corneal dystrophy, cataracts, and glaucoma. The disease or disorders of the posterior segment of the eye in general are retinal or choroidal vascular diseases or hereditary diseases such as Lebers Congenital Amaurosis. The posterior portion of the eyeball supports the retina, choroid and associated tissues.

So far certain treatments, including the topical application of acetylcholine esterase (AChE) inhibitor, have been used with some success to treat ophthalmic disorders caused by dysfunction of eye muscles in the anterior region of the eye.

Acetylcholine, when working on the eye or other smooth muscles of the body is regulated by the natural cholinesterase enzyme which breaks down acetylcholine and thus turns off its parasympathetic effect on muscles. The effect of acetylcholine on the muscles of the eye could be increased either by adding an acetylcholine like drug such as pilocarpine, or by blocking the breakdown of acetylcholine with an AChE drug which inhibits the natural cholinesterase (e.g., a cholinesterase inhibitor). However, the administration of acetylcholine (pilocarpine) results in the side effect of nearsightedness, thus acetylcholine treatment to correct presbyopia has not been effective.

A diminished visual activity may result due to pathologic conditions of tissues or structures located n the anterior segment of the eye or in the posterior region of the eye. Age related macular degeneration (AMD) is one of the specific diseases associated with the posterior portion of the eyeball and is the leading cause of blindness among older people. AMD results in damage to the macula, a small circular area in the center of the retina. Because the macular is the area which enables one to discern small details and to read or drive, its deterioration may bring about diminished visual acuity and even blindness. The retina contains two forms of light receiving cells, rods and cones, that change light into electrical signals. The brain then converts these signals into the images that we see. The macula is rich in cone cells, which give us our central vision. People with AMD suffer deterioration of central vision but usually retain peripheral sight.

There are several types of AMD. The "dry" (non-exudative) type accounts for about 90% of AMD cases. The wet (exudative) form afflicts only about 10% of AMD patients. However, the wet form is a more serious disease than the dry form and is responsible for about 90% of the instances of profound visual loss resulting from the disease. Wet AMD often starts abruptly with the development of tiny, abnormal, leaky blood vessels termed CNVs (chorodial new vessels), directly under the macula. In most patients, this leads to scarring and severe central vision loss, including distortion, blind spots, and functional blindness.

Signs of AMD such as drusen, which are abnormal yellow deposits under the retina, can be present even in patient with normal vision. Drusen look like specks of yellowish material under the retina. They are deposits of extracellular material that accumulate between retinal pigment epithelium (RPE) and Bruch's Membrane. The RPE is a specialized cell layer that ingests used-up outer tips of the rod and cone cells and provides them with essential nutrients (e.g. vitamin A derivatives). Bruch's membrane is a noncellular structure (made mostly of collagen) that separates the RPE from the choroidal circulation below. The choroidal circulation provides the blood supply to the rods, cones and RPE cells. A few small drusen normally form in the human eye, usually after age 40. AMD, in contrast, is almost always associated with a build-up of additional drusen. Drusen occur in two forms. Hard drusen are small, solid deposits that apparently do no harm when present in small numbers. Soft drusen are larger and may have indistinct borders. As soft drusen build up between the RPE and Bruch's membrane, they lift up the RPE and force the two layers apart.

Drusen develop long before the abnormal vessels of wet AMD. Three characteristics of soft drusen are risk factors for developing CNV: The presence of five or more drusen deposits; drusen size greater than 63 micrometers (about the thickness of a human hair); and, the clumping of the drusen deposits. Some evidence suggests soft drusen are instrumental in the spread of abnormal vessels, but whether they stimulate vessel growth (angiogenesis) or simply provide space for them by lifting up the RPE remains unclear.

Two networks of blood vessels nourish the retina, one located on the retinal surface and the other located deep in the retina, external to Bruch's membrane. The abnormal vessels of AMD originate in the lower network of vessels, called the choroidal circulation. These vessels make their way through Bruch's membrane and spread out under the RPE. Blood and fluids leak from them and cause the photoreceptor cells to degenerate and the macula to detach from the cells under it.

Slightly blurred or distorted vision is the most common early symptom of AMD. Visual loss with dry AMD usually progresses slowly while visual loss with wet AMD proceeds more rapidly and may occur over days or weeks. Patients who have wet AMD in one eye are at increased risk of developing CNVs in the other eye. The magnitude of the risk varies, depending on the appearance of the second eye. The risk is greater in eyes with numerous large drusen, with abnormal pigment changes in the macula, and in patients with a history of high blood pressure.

Presently, there are no effective treatments available for visually disabling retinal vascular disease or choroidal vascular disease such as diabetic retinopathy and age related macular degeneration (AMD). The therapeutic strategies for treating diminished or loss of vision caused by the vascular eye diseases vary. Laser photocoagulation is the first effective treatment found for wet AMD. The laser destroys abnormal blood vessels beneath the retinal and seals leaky areas but also destroys the overlying retina. This treatment can inhibit wet AMD's progression, but it cannot restore lost vision and the disease often progresses despite laser therapy. The use of the drug Visudyne (veteporfin) is another approach to treat AMD. This drug belongs to a class of drugs used in photodynamic therapy (PDT), a technique in which light-activated dyes destroy tissue. After an injection, the light-sensitive drug tends to localize in the new choroidal vessels. A low-intensity laser is then focused on the dye-containing CNVs, triggering a chemical reaction that destroys the abnormal vessels. The drug can stabilize vision for a time and slow retinal damage. Other PDT drugs for AMD are currently in clinical testing. However, even with the availability of PDT and conventional laser treatment, patients with the vascular diseases of the eye still have no known effective treatment option and remain vulnerable to sustaining permanent damage to the retinal cells.

The other retinal or choroidal vascular diseases include but not limited to macular cyst, macular hole, solar retinopathy, diabetic retinopathy, branch retinal vein occlusion.

Hitherto it has not been known that a particular regimen of the topical administration of AChE inhibitor can arrest or alleviate the deterioration of vision associated with retinal or choroidal disorders resulting from the pathological conditions of tissues or structures located in the posterior region of the eye. It has also not been known that a particular regimen of the topical administration of AChE inhibitor can be used for the Treatment and Prevention Congenital and Acquired Color Vision Blindness, Treatment of Ocular Hypertension and Glaucoma, Prevention of the Progression of Myopia, Treatment of Strabismus or Squint, Potentiation of Best Visual Acuity, achieving Neuro-protection and for treatment of Aberrations Secondary to Pupil Dilation.

SUMMARY OF THE INVENTION

The present invention is based, at least in part, on the discovery of indirectly improving endogenous acetylcholine levels of eye without adverse effects by using an acetylycholine esterase inhibitor (AChE inhibitor). The method disclosed herein is a physiological method without any need for surgery or laser treatment. The methods use the topical application of acetylcholine esterase inhibitors in very low concentrations but sufficient enough to effectively restore the visual acuity. Specifically, the present invention provides methods for, among other things, the treatment and prevention congenital and acquired color vision blindness, treatment of ocular hypertension and glaucoma, prevention of the progression of myopia, treatment of strabismus or squint, potentiation of best visual acuity, achieving neuro-protection and for correcting aberrations secondary to pupil dilation by topical administration of acetylcholine esterase inhibitors in a concentration effective to improve eye vision in humans without any adverse side effects. Therefore, this invention provides several advantages over prior art methods employed for achieving the same.

DETAILED DESCRIPTION OF THE INVENTION

The invention relates to methods for restoring lost reading or near vision and increasing the amplitude of accommodation in presbyopic patients with emmetropic eyes. The method involves the topical application of an acetylcholine esterase (AChE) inhibitor to the patient. The method can improve near vision without any side effect such as blurring, loss of distant vision or induction of myopia. The medication, applied in appropriate concentration, will allow the patient to achieve near vision, without corrective lenses, which will last several days. Moreover, unlike corrective reading glasses, because of the increase in amplitude of accommodation by practicing the present invention, the individual will be able to focus at many different lengths between the near point and the distant vision. This eliminates the need for bending the head in order to bring an object in line with the lenses of the reading glasses. For the emmetrope, the present invention eliminates for several days the need for corrective reading glasses. For the myopic or hyperopic individual, the present invention eliminates the need for bifocal lenses.

Acetylcholine esterase inhibitors are known to one skilled in the art. There are at least two AChE inhibitor drugs currently approved for clinical use on the eye in the United States. They are (2-mercaptoethyl) trimethylammonium iodide O,O-diethyl phosphorothioate sold as PHOSPOHLINE IODIDE® (Wyeth-Ayerst, Philadelphia, Pa.), and physostigmine (also known as eserine) sold as ANTI-LIRIUM® (Forest Pharmaceuticals, St. Louis, Mo.). PHOSPHOLINE IODIDE is dispensed as eyedrops at a desired potency. PHOSPHOLINE IODIDE of various concentrations, such as for example 0.25%, 0.125%, 0.06% and 0.03% and a pharmaceutically acceptable sterile diluent to dilute the concentrated form of this drug are commercially available. PHOSPHOLINE IODIDE is currently used for glaucoma and accommodative esotropia but there has been no successful use of this drug for presbyopia because of many adverse side effects of the drug especially when used in the standard doses established for glaucoma and accommodative esotropia. As such, PHOSPHOLINE IODIDE is not a preferred drug even to treat glaucoma and accommodative esotropia because of many adverse side effects caused by this drug when it is used in the current regimen of multiple times a day at high concentrations. Some of the side effects known to be caused by the currently recommended doses of this drug (for glaucoma at 0.12 and 0.25 BID) are iris cysts, cataract formation especially anterior subcapsular, posterior syneclial and elevated intraocular pressure.

In the new method the cholinesterase inhibitor, such as phospholine iodide, administered in concentrations many fold more dilute than currently available pharmacological preparations, applied to the eye before sleep will achieve a restoration of the ability to accommodate with none of the unacceptable side effects of the usual pharmacological preparations and without the loss of distance vision. The effect of one administration at night can last for many days and replace the need for corrective reading lenses during that time. The present invention shows that the effective concentration of AChE inhibitor in the composition to treat presbyopia can be very low (for example, as low as at least 0.005% to about 0.0075% of PHOSPHOLINE IODIDE) to be effective. The invention discloses that such a concentration is extremely useful medically. Specifically, this lower dose range is especially useful in providing eye drugs that will contain a concentration of AChE inhibitor that is low enough to be both safe and effective.

The composition administered to the eye should have a pharmaceutically acceptable carrier and a selected AChE inhibitor suspended or dissolved in the carrier. The concentration of AChE inhibitor in the composition administered to the eye and made of administration of the composition in accordance with this invention depends on the type of AChE inhibitor containing composition used for therapy. For example, preferred concentrations of PHOSPHOLINE IODIDE in the PHOSPHOLINE IODIDE containing composition are from about 0.1% to about 0.0019%. Still more preferred concentrations are from about 0.14% to about 0.00375%. More preferred PHOSPHOLINE IODIDE concentrations are from about 0.15% to about 0.005%. Most preferred PHOSPHOLINE IODIDE concentrations are 0.12%, 0.03% and 0.0075%. It is preferred to apply PHOSPHOLINE IODIDE topically to the eyes in the form of eyedrops. Although it is preferred that these solutions with various concentrations of PHOSPHOLINE IODIDE are stored in a refrigerator, they an be stored at room temperature for about two months or even beyond two months without losing their efficacy to restore near vision in presbyopic patients.

A solution containing chlorobutanol (0.55%), mannitol (1.2%) boric acid (0.6%) and exsiccated sodium phosphate (0.026%) can be used as a carrier solution and/or as a diluent for PHOSPHOLINE IODIDE. While this solution is presently sold as a diluent in the kit containing PHOSPHOLINE IODIDE, other pharmaceutically acceptable carriers or excipients that are known to enhance membrane permeability and cellular uptake of the drug can be used with or without modification for application to the eye. Such carriers are known to one skilled in the art.

For the method of the invention to be effective, it is believed that the AChE inhibitor should be administered in such a way that it reaches levels in the eye or ciliary muscle sufficient to improve accommodation. Keeping the eyes such aids in this respect and in a preferred embodiment of the invention, the AChE inhibitors is administered at bedtime. A single topical application of a given AChE inhibitor at bedtime can enhance the strength of the ciliary body muscle and significantly improve the uncorrected near visual acuity in the phakic emmetropic patient for a few days. For example, application of one to two drops of PHOSPHOLINE IODIDE of a selected concentration at bedtime can restore reading vision in presbyopic patients for at least five days. Preferably, the following steps are followed every time AChE inhibitor is applied to the patient. The first step is to read for about 30 minutes. The second step is to administer an AChE inhibitor of a selected concentration. The third step is to sleep. Without wishing to be bound by any theory or explanation, it is believed that the reading for about 30 minutes preconditions eye muscles to respond better to the AChE inhibitor treatments. It takes about 6 to 8 hours of sleep to notice the restoration. If one is awaked in the middle of the sleep, the individual may notice partial effect but after 6 to 8 hours of sleep the effect will be maximized. By the term "bedtime" it is meant that the time when the patient goes to sleep for about 6 to 8 hours, regardless of whether it is during the day or night time.

AChE inhibitor can be administered either to the dominant and/or the non-dominant eye. It is known that usually one eye is "dominant" with respect to the other and with both eyes open the image from the dominant eye will be perceived more than the non-dominant eye. To show that the restoration of near vision is the result of the effect of AChE inhibitor and not because of subjectivity of the dominant eye being preferred over the non-dominant eye, one can treat the weaker or non-dominant eye. By treating the weaker or non-dominant eye, one can show that the weaker eye becomes stronger than the dominant eye in every treated patient and that the restoration of near vision by AChE inhibitor is real, not because of the dominant eye. Also by treating only one eye, the patient can see the improvement and can judge when to apply another dose (within 7–10 days after the first dose) as the non-dominant eye reverts toward seeing like the dominant eye. Additionally, this allows to check for any side effects and making comparison to the untreated eye.

It should be noted that the method of this invention can be successfully used to correct presbyopia in patients having emmetropic eyes with a normal crystalline lens. The method can also enhance the near vision of an individual who has the normal crystalline lens, but has no iris. However, the method may not be successful to correct presbyopia in presbyopic patients with artificial and rigid intraocular lenses (IOL's). IOL's are inserted at the time of cataract surgery and in refractive procedures to make an individual emmetropic.

Accordingly, by practicing the present invention, the near point of distinct vision and also amplitude of accommodation of emmetropic eye can be increased by a single topical application. The near point of an emmetrope can be calibrated into amplitude of accommodation (by the formula D=1/distance in meters to the near point of vision). Increase in amplitude of accommodation can be measured by techniques well known to those skilled in the art. In other words, a suitable dose of AChE inhibitor administered at bedtime can allow the eye to accumulate sufficient stockpiles of acetylcholine by inhibiting acetylcholine esterase activity in the eye and strengthen the ciliary body leading to the improvement in the near point of distinct vision and amplitude of accommodation for sometime. Most middle age emmetropes with presbyopia have near points at arms length (i.e., they can see the near print, only if they move it further and further away from the eye). Reading distance is generally considered to be 33 cm to 35 cm; arms length is greater than this distance. By practicing the method of the present invention, a middle age patient with 20/70 vision at arms length after treatment with AChE inhibitor can obtain 20/20 vision at 12 inches for over five days. To sustain this 20/20 vision at 12 inches beyond this period, the treatment can be repeated in the same fashion. Moreover, by practicing the method of the invention, the restoration of near vision can be achieved in myopes and hyperopic presbyopes who have their distant emmotropic correction with glasses or contact lenses. It eliminates the need for bifocal glasses.

While the detailed discussion of the treatment methods for restoring reading vision in patients suffering from presbyopia disorder has been provided in the text above, the same methods and the concentrations of AChE inhibitor in the compositions described above can also be used to treat other eye disorders as described in the paragraphs below.

The method of the present invention also provides a method for treatment and prevention of dry eye syndrome. The dry eye problem is due to lack of certain components in human tears and is known to those skilled in the art. In dry eye syndrome the tears evaporate too quickly and the patients need supplements of lubricating drops (artificial tears). There has been described treatment of patients with dry eye syndrome using oral pilocarpine. While there has been recovery from the dry eye syndrome, the oral administration of pilocarpine has not been without side effects. Further, such oral administration implicates the entire body in an effort to secure an effect in the eyes. A treatment using AChE inhibitor decreases the tear breakup time (tears stay on the eye longer) without side effects. This invention can reverse the process of old age dry eye syndrome by reactivating the meibomian glands, which supply the oil components to basic tears.

The method of the present invention further provides a treatment method for hyperopia. As described elsewhere, AChE inhibitor restores reading vision in presbyopic patients and increases the accommodative amplitude. The disease hyperopia (farsightedness), maybe prevented by increasing the amplitude of accommodation in the young hyperopes.

The method of the present invention further provides treatment for myopia. Several myopic presbyopics have also noticed a shift in distance correction towards hyperopia or a reduction of their myopia after AChE inhibitor treatment. Therefore, it is believed that treatment with AChE inhibitor can be a treatment to prevent and reverse the disease myopia.

The method of the present invention further provides treatment for amblyopia. Medical dictionary defines amblyopia as "dimness of vision without detectable organic lesion of the eye". By using AChE inhibitor patients can notice an increase of image size after treatment. Their non-dominant eye sees better than their dominant eye. Thus, AChE inhibitor treatment can be used in accordance with the present invention in relative or absolute amblyopics to improve inherent weakness by magnifying image.

The method of the present invention further provides treatment for glaucoma. It is known that there is an age correlation between the most common variety of glaucoma (open angle glaucoma) and presbyopia. There are glaucoma agents that actively stimulate the ciliary body to achieve pressure reduction in glaucoma. However, there are theories that during the treatment for glaucoma, lens proteins disintegrate and/or the ciliary body secretes proteins abnormally (pseudo exfoliation syndrome). But by keeping the ciliary body active as in the treatment of presbyopia can keep pressures at a normal level without needing shock therapy to the ciliary body as in high doses of glaucoma medicines. By keeping the lens active as in treatment of presbyopia prevents the ciliary body from abnormally secreting and prevents the disintegration of lens proteins.

The method of the present invention still further provides treatment for cataracts. It is known that there is an age correlation of presbyopia and cataract formation. Currently, AChE inhibitor (PHOSPHOLINE IODIDE) is being used to treat glaucoma and accommodative estropia and the anterior sub capsular cataract formation is a side effect of prior art therapeutic doses. For three years, there was no cataract formation in the treated eye versus the non-treated eye. By practicing the method of the present invention, one can keep the lens flexible through accommodation. This will prevent the disintegration of lens proteins (cataract formation). To prevent cataract formation in both eyes, AChE inhibitor should be applied to both eyes. Simply by practicing the methods disclosed herein during the course of last three years, it has been found that, there was no disintegration of lens proteins and cataract formation in the treated eye as opposed to the non-treated eye.

By practicing the method of the present invention, alleviation of diminished visual acuity due to, for example, macular cyst, macular hole, solar retinopathy, diabetic retinopathy, branch retinal vein occlusion and AMD can also be achieved. By "restoration or alleviation of diminished visual acuity", it is meant that any significant improvement in vision of a patient suffering from blindness or poor vision.

These diseases in human patients are usually diagnosed by opthalmologistis or other physicians familiar with etiology of eye, by means of special photography of the retina. In a typical diagnostic procedure, flourecein angiography, the physician injects a fluorescein vegetable- base dye into a patient's blood. The patient's pupil is also dilated by administering pupil dilating drugs (mydriatic) to the eye. The physician then takes a series of photographs of the retina, using a light source at a particular excitation wavelength so that it causes any leakage of fluid of the drug from the patient's retinal and choroidal vasculature to emit fluorescent light at a different wavelength. The physician then analyzes the series of photographs of the retina to determine the presence and concentration of leakage. If present at abnormal levels as determined a physician skilled in this area, these abnormal levels of fluorescent leakage indicate the presence or onset of a particular retinal or choroid vascular disease.

By practicing the method of the present invention, the disease condition of the yea is at least stabilized without further deterioration of the tissues.

The structure, cellular anatomy physiology, biochemistry and other details of the eye are provided in various ophthalmological and medical school texts that focus specifically on the eye and diseases of the eye e.g. Dwanes Textbook of Ophthalmology, the American Academy of Ophthalmology Clinical Science Course, etc. The practicing physicians in this art can readily determine anatomical structures of a normal and diseased human eye whether the disease be in the anterior or posterior region of the eye ball. Once a human patient is diagnosed as suffering from a disease such as those described in the above paragraph, an amount of a acetylcholine esterase inhibitor containing composition sufficient to provide a therapeutic benefit is administered.

Acetylcholine esterase inhibitors are known to one skilled in the art. There are at least two AChE inhibitor drugs currently approved for clinical use on the eye in the United States. They are (2-mercaptoethyl) trimethylammonium iodide O,O-diethyl phosphorothioate sold as PHOSPOHLINE IODIDE® (Wyeth-Ayerst, Philadelphia, Pa.), and physostigmine (also known as eserine) sold as ANTI-LIRIUM® (Forest Pharmaceuticals, St. Louis, Mo.). PHOS-PHOLINE IODIDE is dispensed as eyedrops at a desired potency. PHOSPHOLINE IODIDE of various concentrations, such as for example 0.25%, 0.125%, 0.06% and 0.03% and a pharmaceutically acceptable sterile diluent to dilute the concentrated form of this drug are commercially available. PHOSPHOLINE IODIDE is currently used for glaucoma and accommodative esotropia. As such, PHOS-PHOLINE IODIDE is not a preferred drug even to treat glaucoma and accommodative esotropia because of many adverse side effects caused by this drug when it is used in the current regimen of multiple times a day at high concentrations. Some of the side effects known to be caused by the currently recommended doses of this drug (for glaucoma at 0.12 and 0.25 BID) are iris cysts, cataract formation especially anterior subcapsular, posterior synechiae and elevated intraocular pressure.

In the new method, the cholinesterase inhibitor, such as phosphoholine iodide, administered in concentrations many fold more dilute than currently available pharmacological preparations, applied to the eye before sleep will achieve alleviation of the deteriorated or deteriorating vision with none of the unacceptable side effects of the usual pharmacological preparations and without the loss of peripheral vision. The effect of one administration of the inhibitor can last for many days. The present invention shows that the effective concentration of AChE inhibitor in the composition to treat diseases associated with the posterior region of the eye can be very low (for example, as low as at least 0.001% to about 0.0075% of PHOSPHOLINE IODIDE) to be effective. The invention discloses that such a concentration is extremely useful medically. Specifically, this lower dose range is especially useful in providing eye drugs that will contain a concentration of AChE inhibitor that is low enough to be both safe and effective. For example, application of a drop of 0.03% PHOSPHOLINE IODIDE followed by a drop of suitable diluent (e.g., artificial tear) is not incompatible with the drug.

The composition administered to the eye should have a pharmaceutically acceptable carrier and a selected AChE inhibitor suspended or dissolved in the carrier. The concentration of AChE inhibitor in the composition administered to the eye and the method of administration of the composition in accordance with this invention depends on the type of AChE inhibitor containing composition used for therapy. For example, preferred concentrations of PHOSPHOLINE IODIDE in the PHOSPHOLINE IODIDE containing composition are from about 0.25% to about 0.001%. More preferred PHOSPHOLINE IODIDE concentrations are from about 0.15% to about 0.005%. Most preferred PHOSPHOLINE IODIDE concentrations are about 0.12%, 0.03% and 0.0075%. It is preferred to apply PHOSPHOLINE IODIDE topically to the eyes in the form of eyedrops. Although it is preferred that these solutions with various concentrations of PHOSPHOLINE IODIDE are stored in a refrigerator, they an be stored at room temperature for about two months or even beyond two months without losing their efficacy to restore near vision in presbyopic patients.

A solution containing chlorobutanol (0.55%), mannitol (1.2%) boric acid (0.6%) and exsiccated sodium phosphate (0.026%) can be used as a carrier solution and/or as a diluent for PHOSPHOLINE IODIDE. While this solution is presently sold as a diluent in the kit containing PHOSPHOLINE IODIDE, other pharmaceutically acceptable carriers or excipients that are known to enhance membrane permeability and cellular uptake of the drug can be used as diluents with or without modification for application to the eye. Such carriers are known to one skilled in the art.

In a preferred embodiment of the invention, the AChE inhibitor is administered at bedtime. A single topical application of a given AChE inhibitor at bedtime can enhance visual acuity in the phakic emmetropic patients as well as in pseudophakic patients for a few days. For example, application of one to two drops of PHOSPHOLINE IODIDE of a selected concentration at bedtime can alleviate the diminished vision of the patients for at least five days. Preferably, the following steps are followed every time AChE inhibitor is applied to the patient. The first step is to read for about 30 minutes. The second step is to administer an AChE inhibitor of a selected concentration. The third step is to sleep. Without wishing to be bound by any theory or explanation, it is believed that the reading for about 30 minutes preconditions eye muscles and visual pathway to respond better to the AChE inhibitor treatments. It takes about 6 to 8 hours of sleep to notice the restoration. If one is awaken in the middle of sleep, the individual may notice partial effect but after 6 to 8 hours of sleep the effect will be maximized. By the term "bedtime" it is meant that the time when the patient goes to sleep for about 6 to 8 hours, regardless of whether it is during the day or night time. The composition is administered at bedtime, i.e., it is administered just before the patient goes to sleep for about 6 to 8 hours.

AChE inhibitor can be administered to the eye with the disease. It should be noted that the method of this invention can be successfully used to treat diminished visual acuity in phakic as well as pseudophakic patients. The method can also enhance visual acuity of an individual who has no iris. Of particular interest is that this method can be successfully used to treat patients with artificial and rigid intraocular lenses (IOL's). IOL's are inserted at the time of cataract surgery and in refractive procedures to make an individual emmetropic by clear lens extraction. Further, it should be noted that the diminished visual acuity can occasionally be alleviated also in contralateral eye (or untreated eye) to some degree.

Accordingly, by practicing the present invention, one can achieve a definite, measurable gain in visual acuity in patients with retinal vascular or choroidal vascular disease or other known diseases of posterior segment of the eye when administered with the acetylcholinesterase inhibitor, in the dilution and the manner outlined above. Increase in visual acuity can be measured by techniques well known to those skilled in the art. Although the mechanism of action is unknown, it is believed that a suitable dose of AChE inhibitor administered at bedtime may allow the eye to accumulate sufficient stockpiles of acetylcholine by inhibiting acetylcholine esterase activity in the eye and strengthen the eye muscles leading to the normal perfusion of the blood to the posterior region of the eyeball particularly choroid blood vessels. Retinal and choroidal function and health are dependant on normal perfusion of these tissues.

The method of the present invention also provides for treatment and prevention of congenital and acquired color vision blindness. Color vision is made possible by the cones of the retina, which are also responsible for central vision or best visual acuity. Color vision is measured by using standardized color plates, as in ISIHARA color plates.

In acquired color vision loss, as in retinal diseases such as Stargards Disease, juvenile macular degeneration, color vision can be restored in both eyes by a drop of AChE inhibitor in only one of the color-blind eyes.

In patients with senile macular degeneration, there can be loss of color vision together with the loss of central vision. Color vision loss will precede or coexist with central vision loss. In Stargard's Disease, color vision loss may precede central vision loss by several years. In dry senile macular degeneration and diabetic retinopathy, color vision loss precedes and coexists with central vision loss. Patients complain of vision diminution. Color vision may be markedly decreased, although central vision has dropped slightly. Loss of color vision is a bad sign, as it represents diffuse or widespread damage of the cones. Color vision loss portends more central vision loss. Finally, with advanced disease, visual acuity <20/400, color vision may be maximal only up to 30 percent. The exception to this rule is loss of vision with macular hole-formation. These patients may have very reduced visual acuity, but color vision remains normal. Macular-hole disease represents focal damage of the central macula, the fovea. The para-foveal regions remain with healthy cones for color vision at 100 percent.

Application of a drop of AChE inhibitor 0.015% can restore color vision. The mechanism of action is unknown, but AChE inhibitor probably works directly on deenervated damaged cones to reenervate them. The color-blind cones appreciate color again, and this improvement in color vision correlates with improved visual acuity. This process reverses the process of juvenile and old age color blindness of the eye.

The method of the present invention also provides the treatment of ocular hypertension and glaucoma. Ocular hypertension is elevated intra-ocular pressure without optic nerve damage and blindness. The ciliary muscle controls the outflow of aqueous humor of the eye, preventing the build up of intra-ocular pressure (IOP) in the eye (glaucoma). When AChE inhibitor 0.03% is given to patients with glaucoma previously controlled with glaucoma drops (e.g. timoptic, alphagan, or xalatan), patients can be equally well controlled by less frequent administration of AChE inhibitor (0.03% of AChE inhibitor drops). When applied twice a week, as compared to daily or twice daily of the other medications, there is equal control of the IOP. There is no progression of the glaucoma as documented by no further damage to the optic nerve or loss of visual field.

There are distinct advantages to this new method in terms of compliance, tolerance, and economy. It is documented that the compliance of patient to take medications goes up with the fewer times the medication needs to be taken. It is also understood that there is less tolerance, or loss of effect of a medication, when the medication is taken infrequently. There is more tolerance of other glaucoma medications because they are taken so frequently. Lastly, the fewer the times a medication is used, the more cost effective the medication will be. AChE inhibitor has been used for many years, up until recently, to treat glaucoma. However, frequent high dosing has led to unacceptable patient compliance and to lack of efficacy (tolerance).

What is claimed is a new method for treatment of glaucoma, which would allow weekly and biweekly dosing. Generally, IOP elevation has no symptoms and cannot be internally monitored by the patient. However, presbyopic patients taking AChE inhibitor notice that their needs for accommodation enhancement comes on the fourth day or at about the same day the intra-ocular pressure begins to be elevated. They can monitor their ciliary muscle function through accommodation and thus indirectly they can monitor their IOPs.

The method of the present invention also provides for the prevention of the progression of myopia. When given to several patients with progressive myopia, the progression of the myopia was prevented. By progressive myopia is meant the progressive increase in glass prescription nearsightedness by 0.5–0.75 diopters in less than 1 year time for over three consecutive years. The mechanism for myopic progression is unknown and has genetic and environmental influences. How AChE inhibitor effects the prevention of progression of myopia is unknown. What is known is that myopic patients frequently have abnormally large pupils versus the average patient. Young (20 yr old) myopic patients, having undergone RK or Lasik, may have as poor accommodation function as the 40-year-old presbyopic patient. Biochemically, acetylcholine governs both the pupil size and accommodation. Empirically, you may reason that an endogenous lack of acetylcholine in the eye may be a cause for myopia. The present invention allows for higher levels of acetylcholine indirectly by AChE inhibitor.

The method of the present invention also provides for the treatment of strabismus or squint. AChE inhibitor also effects the external muscles of the eye or extra-ocular muscles (EOMS). The two eyes are held in check on a straight line by fusion, which is a function of the strength of the EOMs. Abnormal eye position, whether eso or exo (in or out) or hyper or hypo (up or down), is measured in prism diopters. The eye muscles (EOMs) keep the eye aligned and have a potential strength in keeping alignment. These measurements of fusional amplitude are also measured in prism diopters. Measuring fusional amplitudes in presbyopic patients before and after treatment of the presbyopia shows an average gain of 5–10 prism diopters horizontally and 1–2 prism enhancement vertically. Diplopia or double vision occurs when an acquired paralysis of an EOM occurs. Whether exo, eso, hyper, or hypo, these misalignments of the eye are measured in prism diopters. When treating patients with a paralytic muscle with AChE inhibitor, the amount of the deviation is reduced on the first day of treatment versus the pretreatment measurements. The fact that the enervation of the EOMs is through acetylcholine and that paralytic EOM muscles become hypersensitive to acetylcholine concentrations accounts for the reason AChE inhibitor works here.

The method of the present invention also provides for the potentiation of best visual acuity. AChE inhibitor also has the effect of making normal vision hyper or super normal, i.e., the base line normal vision (the best corrected vision) or seemingly perfect vision is potentiated after the treatment with AChE inhibitor. When normal patients with 20/20 best corrected or uncorrected vision are given AChE inhibitor as in presbyopia, best visions may improve to better than 20/20 or 20/15 to 20/10 vision. This mechanism of action may be through a magnification effect of the crystalline lens of the eye. Some patients report a magnification of image in the treated eye versus the non-treated eye. This hyper effect is also seen in pseudophakia, where the crystalline lens has been replaced by an IOL intraocular lens. The mechanism may be explained on this potentiation on the retinal tissue itself. The retina has a conglomeration of ganglions and neurons, which communicate with each other through acetylcholine and their actions are potentiated by AChE inhibitor.

The method of the present invention also provides for the phenomena known as neuro-protection. The recent literature is full of pharmaceuticals that may protect the nerves of the eye in glaucoma e.g. the optic nerve and the neurons leading into the optic nerve or nerve fiber layer. The agents that cause neuro toxicity or retinal toxicity of the eye are ischemia, or poor perfusion of blood flow, and poisons. Poisons are exogenous like alcohol or tobacco or endogenous as in Stargards Disease or Congential Lebers Amaurosis and Retintitis Pigmentosa. The endogenous poisons are genetic or bad gene related.

Whether ischemia or toxin, the final blow to nerve preservation is at the neural synapses or connections between individual nerves. In the eye, acetylcholine governs 99% of synaptic connections between neurons and may become sacrificed by ischemia and toxins. However, AChE inhibitor allows protection of synaptic spaces as it's nicotinic properties allow for the excess acetylcholine to keep the nerve function working and also to repair potentially damaged synapses and restore and prevent loss of color vision, central visual acuity and peripheral vision. The muscanic properties of AChE inhibitor and its effect on the smooth muscles of arterioles allows for the relaxation of arterioles, relief of ischemia and better perfusion of eye tissues, further assuring neuro protection. In Stargards Disease, the neuro-protection occurs when the AChE inhibitor interferes with the activity of the endogenous poison. For example, one patient with deteriorated central and color vision noticed that when using AChE inhibitor on a weekly regimen, there was a reversal of the improved central and color vision toward the end of the fourth day. Giving AChE inhibitor every $4^{th}$ day allowed neuro-protection of the visual pathway with out the cascading loss of best visual acuity and color vision. In macula degeneration and diabetic retinopathy, AChE inhibitor improves visual acuity and color vision and provides neuroprotection to further visual loss. Patients are strongly recommended to use their medications but because of the age of many of the patients sometimes they stop or forget to take their meds with the loss of this neuro-protection. Their visions can be improved when beginning their medications but sometimes not to the degree of the original improvement.

The present invention also provides for the treatment visual aberrations secondary to pupil dilation. The pupillary constriction is by the action of AChE inhibitor on the sphincter muscle of the iris, another intra ocular muscle. Patients suffering from traumatic mydriasis (surgical or non-surgical), subluxed intraocular lens, IOL, and central corneal opacities are improved with mild miosis that is sustained with AChE inhibitor. Many patients with myopia, (before and after Lasik) suffer with myopic nocturnal mydriasis and patients with psuedophakia (status post cataract extraction with IOL) complain of difficulty with night vision especially while driving a motor vehicle. They also get relief from these vision problems after the application of AChE inhibitor. Pilocarpine is unacceptable because of the acute non-sustained miosis, which is accompanied with change of refraction and blurring of vision.

The topical administration of acetylcholine esterase inhibitors are applied to one or both eyes depending on the type of treatment. For the treatment and prevention congenital and acquired color vision blindness, treatment of ocular hypertension, glaucoma and progressive of myopia and potentiation of best visual acuity it can be applied in one or both eyes. For the treatment of strabismus or squint acetylcholine esterase inhibitors should be applied to the eye with paralysis of muscle. For achieving Neuro-protection acetylcholine esterase inhibitors should be applied to the eye in need of neuroprotection, and for treating aberrations secondary to pupil dilation, acetylcholine esterase inhibitors should be applied to the eye with the dilated pupil. Color vision blindness, ocular hypertension, progression of myopia Strabismus or pupil dilation are referred to herein as disorders.

EXAMPLES

The examples below are carried out using standard drug administration techniques, that are well known and routine to those of skill in the art, except where otherwise described in detail. The examples are illustrative, but does not limit the invention. These examples illustrate among other things (1) the alleviation of diminished visual acuity in humans suffering from diseases or disorders of the anterior and/or posterior segment(s) of the eye and (2) potentiation of baseline normal vision by topical administration of an AChE inhibitor to the eye.

1. Treatment of Emmetropes with Presbyopia

After a comprehensive examination of patients, seven emmetropes with presbyopia were identified for the treatments. The mean age of the patient was 48.5 years. These emmetropic patients were treated with (2-mercaptoethyl) trimethylammonium iodide O,O-diethyl phosphorothioate sold under the trademark PHOSPHOLINE IODIDE. Each time only one drop of one of the three different doses of 0.12%, 0.3% and 0.0075% concentrations were topically applied to the non-dominant eye of each patient. Patients were administered medication to the non-dominant eye at bedtime after reading for 30 minutes. The treatment was repeated at five to seven day intervals.

Pre-treatment uncorrected near vision was 20/50 to 20/70 and mean pre-treatment amplitude of accommodation was 2.5 diopters. Examination of patients on days one to five showed considerable increase in near visual acuity from 20/20 to 20/25. The amplitude of accommodation improved to 2.5 times. On the first day after the treatment, patients noticed a slight decrease of light sensitivity in dull illumination. This sensitivity subsided by the following day. There was a sustained accommodative effect from the first five days even though there was some tapering of the effect on day six or seven. Even on day seven, the amplitude of accommodation was significantly greater (1.5 times) than that of day zero. Near vision was restored in this manner without major side effects. Patients noticed that they regained the ability to thread a needle, suffered less computer strain and experienced fewer headaches. Patients could read newspaper print without corrective lenses for near vision.

2. Treatment of Patients with Age Related Macular Degeneration, Macular Cyst, Macular Hole, Solar Retinopathy, Diabetic Retinopathy, Branch Retinal Vein Occlusion, or Lebers Congenital Amaurosis Twenty nine patients (34 eyes) were studied with ages 42 to 92. Etiology varied from diseases of the choroidal vasculature such as dry AMD and wet AMD, macular hole, Solar Retinopathy, Lebers Congential Amaurosis and retinal vascular diseases such as Diabetic Retinopathy with Maculopathy, and Retinal Vascular Occlusion. All of the patients studied showed restoration of vision. Patients included both phakic and pseudophakic. Medications were applied similarly at bedtime after about 20 minutes of reading once a week. Patients monitored their visions and if there was a regression of vision midweek, the dose was made twice weekly. A drop of PHOSPHOLINE IODIDE at a concentration of 0.03% with or without a drop of an artificial tear as a diluent was the regimen. Two patients stopped their medications and lost the effect (patient 5 and 9). One patients began using the medication in the morning and likewise lost the effect (patient 12). Another patient (patient 14) administered the drug at dinner time and lost the effect. These four patients had their visions restored on restarting the medications at bedtime after reading for about 20 minutes. The vision restoration is immediate and generally noticed on the first day or week of treatment. The medication was given unilaterally, that is to the diseased or more diseased eye. Most patients showed a constriction of the pupil in both eyes although the medication is given in only one eye. Pupil constriction is not necessary for vision improvement, as seen in patient 29 who is aniridic (no iris). Occasionally, patients noticed an improvement of vision also in the opposite or contralateral eye. That is, patients with bilateral disease, when the poorer of the two eyes is treated, the untreated better eye can show an effect of vision improvement. All patients were given pre treatment comprehensive examinations and had documented retinal and/or choroidal vascular disease by flourescein angiography.

Patient 1: This patient was pseudophakic and diagnosed as suffering from wet AMD. Prevision was counting fingers (CF), pinhole vision no help (PHNH). At one foot, vision was 1'/400. On day one, vision improved to 1'/100 or to 3'/400. At one week vision was 6'/400 and at two weeks 20'/300. At 8 weeks, distant vision was 20/400, 20/300 and near vision 20/70. At 3 months vision was 20/200-1.

Patient 2: This patient was pseudophakic and diagnosed as suffering from dry AMD. Prevision 20/40-2 PHFH. At one week 20/30 ph 20/25. At 8 weeks vision was 20/30-.

Patient 3: This patient was pseudophakic and diagnosed as suffering from retinal vascular occlusions. Prevision CF PHNH 3'/300. At one week vision improved to 3'/70. At week two vision was 3'/25 or 6'/400 and near vision 20/70.

Patient 4: This patient was pseudophakic and diagnosed as suffering from dry AMD. Prevision 20/70- near vision 20/40. At one week vision improved to 20/50-1 near vision 20/25. At two weeks vision was 20/40-. At 4 weeks vision was 20/40-2, near vision 20/25.

Patient 5: This patient was pseudophakic and diagnosed as suffering from dry AMD and preretinal fibrosis. Prevision was 20/50-2. At one week vision was 20/40 PH 20/30- and at two week 20/30. At 8 weeks vision remains 20/30. At 3 months BK has stopped medusa for 10 days and vision was 20/40-3.

Patient 6: This patient was pseudophakic and diagnosed as suffering from dry AMD s/p laser for wet AMD. Prevision was 20/25+2. At one week vision 20/20-1. At week three vision was 20/20-1.

Patient 7: This patient was pseudophakic and diagnosed as suffering from early or pre AMD. Prevision was 20/30+2. At one week vision was 20/25+1 and at two week 20/20. At week four vision was 20/15-1. At three months vision was 20/20-1, near vision 20/20.

Patient 8: This patient was phakic and diagnosed as suffering from dry AMD. Prevision was 20/25. At one week vision was 20/20. At week two vision was 20/15-1.

Patient 9: This patient was pseudophakic and diagnosed as suffering from dry AMD. Prevision was CF PHNH. At one week vision was 20/200. At two weeks CF the patient stopped taking medications. At week three on medications vision returned to 20/200. The patient admits to a marked improvement of peripheral. At six weeks vision was 20/200 and near vision 20/50.

Patient 10: This patient was phakic and diagnosed as suffering from macular holes both eyes. Best vision was right eye 20/100 PH 20/100+1, near 20/70, left eye 20/100-1 PHNH., near 20/70. At one week right 20/70- near 20/30, left 20/70-1 near 20/70. At three months vision was 20/70-2 near uncorrected 20/50- right (last drop right was one week), left was 20/70-1 with a near uncorrected 20/30 (last drop was last night). Binocular near vision was 20/25- and patient is reading for the first time five years+.

Patient 11: This patient was pseudophakic and diagnosed as suffering from diabetic retinopathy with maculopathy. Prevision was 20/70 PHNH near 20/50. At one week no effect. At two weeks vision 20/40-1 near 20/25. At six weeks vision remained stable at 20/40-1T.

Patient 12: This patient was pseudophakic and diagnosed as suffering from dry AMD. Prevision was CF PHNH or 1'/400. At one week vision was 3/400, two weeks 6'/400 and at three weeks 20/300. For the next four weeks the patient began using drops in the am. At 8 weeks vision was CF PHNH, 1/400' snf and at 9 weeks 3/400. At 11 weeks vision was 6 feet/200.

Patient 13: This patient was pseudophakic and diagnosed as suffering from dry AMD. Prevision was 20/100-1 PHNH near vision was 20/40-. At week one vision was 20/50-1 and near vision 20/25.

Patient 14: This patient was pseudophakic and diagnosed as suffering from dry AMD. Prevision was 20/100 PHNH. At one week vision was 20/50. At two weeks, vision was 20/40-3. The patient began using drops at dinner time and lost effect although pupil was constricted at week four.

Patient 15: This patient was pseudophakic and diagnosed as suffering from wet AMD left eye and dry AMD right. Prevision was 20/40+ PHNH right and CF PHNH 1'/400 left. At week one, vision was 1/100- with noticeable increase in peripheral vision. The patient could read the time on his watch with the left eye. At week two, vision was 20/400+. (left eye) right eye at week one, vision was 20/30+1 and at week two, vision 20/20-.

Patient 16: This patient was pseudophakic and diagnosed as suffering from dry AMD right and wet AMD left. Prevision was 20/25- PHNH right and 20/200 PHNH. At one week vision was 20/20-2 right and 20/100 left. At one month vision was 20/20-2 and 20/200 left.

Patient 17: This patient was phakic and diagnosed as suffering from solar retinopathy from staring into the sun. Prevision was 20/30+ PLNH. At one week vision was 20/25. At three weeks vision was 20/25 (no eye drops for 8 days).

Patient 18: This patient was pseudophakic and diagnosed as suffering from BRVO (Branch Retinal Vein Occlusion). Prevision was 20/400 PHNH. At one week vision was 20/200 and at week two vision was 20/100-. Even at week one, patient noticed a marked increase in vision. At week two, vision was 20/100 (slow) near vision 20/70.

Patient 19: This patient was phakic and diagnosed as suffering from mild dry AMD right<left. Prevision was 20/20-1 right 20/25-3 PHNH left. At one week left remained at 20/25-3 but at two weeks vision was 20/20-1 left.

Patient 20: This patient was pseudophakic and diagnosed as suffering from dry AMD right<left. Prevision was 20/25-1, +1 right and 20/25-3 left, PHNH. At one week left eye was 20/25 and as strong as the right eye. At week two vision was 20/20-1 and stronger than the right. At four weeks both eyes were treated and vision was 20/20 right 20/20 left.

Patient 21: This patient was phakic and diagnosed as suffering from Lebers Congenital Amaurosis. Prevision was 20/CF or 6'/400 PHNH right, LP (light perception) left. At one week s vision was 6'/100 right and HM (hand motion). At week two, vision improved to 20/400 right, HM left. At week three, vision improved to 20/200-1 right, and remained at HM left. At six weeks vision was 20/200 with a near vision 20/70.

Patient 22: This patient was phakic and diagnosed as suffering from diabetic retinopathy. Prevision was 20/200right and 20/200 slow left eye PHNH. The weaker of the two eyes or left eye was treated. At one week vision was 20/200 right 20/100-1 left. At week three both eyes were treated and vision was 20/100 right, 20/100 left.

Patient 23: This patient was pseudophakic and diagnosed as suffering from AMD and is status post visudyne laser. Prevision was HM hand motion. On the first day vision was 1'/400 and at one week 1'/100 and he reports a significant improvement of peripheral vision. At week three vision was 8'/400.

Patient 24: This patient was pseudophakic and diagnosed as suffering from dry AMD with prevision 20/40+ PHNH. At two weeks vision was 20/25. At two months the patient stopped meds and vision was 20/40. At 10 weeks vision returned to 20/25.

Patient 25: This patient was pseudophakic and diagnosed as suffering from dry AMD and occult wet AMD with prevision of 20/30+ PHNH. At one day vision was 20/20- and this has remained through 2 months.

Patient 26: This patient was pseudophakic and diagnosed as suffering from dry AMD with prevision of 20/30-1+3 PHNH. At one day vision was 20/20-2+3.

Patient 27: This patient was pseudophakic and diagnosed as suffering from pre retinal fibrosis with a prevision 20/40- PHNH. At one day vision was 20/40+ and at one week 20/25-2.

Patient 28: This patient was phakic and diagnosed as suffering from macular hole right eye and mild dry AMD and early cataract left. Previson was CF 10/400 PHNH with near 20/400+ right and 20/30 PHNH. Near 20/25 left. Medication was applied to the right only. At day one vision was 20/400 right with near vision 20/100 in the right eye. The left eye improved to 20/20- at distance and 20/20 at near.

Patient 29: This patient was pseudophakic and diagnosed as suffering from dry AMD right<left. The left eye has aniridia (NO IRIS). Prevision was 20/30-1 PHNH no help right eye and 20/100- PH 20/70-1 left eye and a near vision of 20/70 left. The left eye was treated first initially. At one week vision was 20/70- and at 4-wks 20/70. Both eyes were treated and at two months vision was 20/25 right and 20/50 left. Near vision left improved to 20/30.

3. Treatment of Patients with Loss of Color Vision

Patient AF 25 year old (yo) has been blind from Stargards Disease for five years. The patient noticed that her color vision was changing at age 15 and preceded her blindness by several years. She was treated at the Wilmer Eye Institute (John Hopkins University) and confirmed to have advanced color vision and central vision deficiency. When seen in our clinic in May 2001, color vision was 0% OD (right eye), and 10% OS (left eye). Central vision was 1/400 OD and 20/400 OS. After one drop of (0.015%) AChE inhibitor to the right eye color vision improved to 70% OD and 100% OS. At three months, best vision is 20/100-1 OD and 20/200 OS and s color vision is 90% OD and 100% OS.

Patient OJ with macular degeneration noticed a decrease in vision in the right eye (previously only the left eye was treated). Color vision OD was 50% and central vision 20/40-. After one drop of (0.015%) AChE inhibitor color vision was 80% and central vision improved to 20/30.

Patient JL, 18 year old, has congenital color vision. Color vision was 0% OU (both eyes). After one drop of (0.015%) Ache inhibitor, color vision improved to 10% OD, 0% OS.

4. Treatment of Ocular Hypertension and Glaucoma

Patient Fr B who has hyperopia and glaucoma and who was treated with Timoptic XE every bedtime had no relief but when treated with 0.03% AChE inhibitor every $4^{th}$ bedtime, IOP (intraocular pressure) was maintained in the normal range, (<18), without evidence of progression of disease. His hyperopia and presbyopia were also corrected on this regimen and he could read at distance and near without glasses at the age of 64.

Patient HE has glaucoma and psuedophakia treated with alphagan twice daily. When treated with AChE inhibitor (0.03%) every $4^{th}$ bedtime, IOP was maintained in the normal range. Best corrected vision improved from 20/30, 2030 to 20/25, 20/25 (Potentiation of Best Visual Acuity). Night time vision while driving improved secondary to pupillary constriction (Aberrations Secondary to Pupil Dilation).

Patient CO has ocular hypertension as well as macular holes. Pre treatment IOP was 25 OD 24 OS. After treatment with AChE inhibitor (0.03%) for Macular holes, IOP was maintained in the normal range (<18 ).

5. Prevention of the Progression of Myopia

Patient KS, a 12 yo with progressive myopia for the past 3–4 years. Pre vision was 20/100 OU uncorrected and with correction =2.50 best vision was 20/20–. AChE inhibitor (0.03%) was given every weekend (Friday OD/ Sunday OS, and uncorrected vision improved to 20/30– OU. Refractions at one year remained at –2.50 without progression of the myopia although the patient went without her glasses seeing in the 20/30– range.

6. Treatment of Strabismus or Squint

Six presbyopic patients were tested for horizontral fusional amplitudes using base out prisms and vertical fusional applitudes using base down prisms of the phoropter rotary prism. After AChE inhibitor (0.015%) fusional applitudes increased horizontally and vertically as stated above. Patients admitted to less eye fatigue during and after driving for extended periods and while using the computer and performing their usual daily activity. Their eyes ached less at the end of the day.

Patient D McD developed a paralytic strabismus in the right eye. Examination revealed a partial right medial rectus palsy. There was a XT (Exotropia) of 35 base in primary gaze, which increased to 50 XT on left lateral gaze and reduced to ortho (no deviation) on right lateral gaze. AChE inhibitor (0.015%) was given to the effected right eye and the next day the XT measured 20 base out prism in primary gaze.

7. Potentiation of Baseline Normal Vision

Patient GN is a 50 year old presbyopic with a best corrected prevision of 20/15–2, 20/15–1. After treatment with AChE inhibitor (0.015% or 0.0225%), best vision improved to 20/15+3, 20/10–1.

Patient HM is a 70 year old with psuedophakia with best prevision of 20/30+2. After AChE inhibitor (0.015%) best vision was 20/20+.

Patient FH is a 48 year old presbyopic with best corrected prevision 20/15–1. After AChE inhibitor, (0.0225%) best corrected vision was 20/15+2.

8. Treatment for Neuroprotection of Eyes

Patient 11, AV, is a 75 year old with Diabetic Retinopathy with a dry macula. Pre vision was reduced to 20/70. After 3 weeks with AChE inhibitor (0.015%) vision was 20/40. His eye was neuro-protected until he stopped his meds and vision dropped to 20/50–. Upon restarting medications vision became 20/50+1 and has remained here at this level.

9. Treatment of Visual Aberration Secondary to Pupil Dilation

Patient MC had traumatic mydriasis after intra ocular and retinal surgery. Pupil measured 8 mm in the eye versus 3 mm in the normal eye. After AChE inhibitor (0.015%) once weekly pupils were 4 mm and 3 mm and there was less glare in the daytime and at night. The patient's referring ophthalmologist had put the patient on pilocarpine, which needed to be used 4 times daily to get relief from the visual aberrations.

Patient DB had large myopic pupils and is status post Lasik vision correction. Driving at night was still difficult from the glare and which problem was eliminated with AChE inhibitor (0.015%) once weekly.

Patient BB had psuedophakia with IOL subluxation. The patient complained of distortion of vision, day and night from the edge of the IOL. Rather than reposition the lens, AChE inhibitor (0.015%) was given once weekly to constrict the pupil over the edge of the optic of the IOL. The patient's vision became acceptable and another surgery was avoided.

While this invention has been described with reference to specific embodiments, those of ordinary skill in the art will understand that variations in these methods and compositions may be used and that it is intended that the invention may be practiced otherwise than as specifically described herein. Accordingly, this invention includes all modifications encompassed within the spirit and scope of the invention as defined by the claims.

What is claimed is:

1. A method of treating a human patient suffering from color vision blindness, the method comprising topically administering to both eyes of the human patient or to an eye affected with said color vision blindness, an amount of a acetylcholine esterase inhibitor containing composition sufficient to provide a therapeutic benefit.

2. The method of claim 1, wherein the composition is administered at bedtime.

3. The method of claim 2, wherein said inhibitor is (2-mercaptoethyl) trimethylammonium iodide O,O-diethyl phosphorothioate.

4. The method of claim 3, wherein said (2-mercaptoethyl) trimethylammonium iodide O,O-diethyl phosphorothioate is present at a concentration of 0.001% to 0.25%.

5. The method of claim 4, wherein the concentration of (2-mercaptoethyl) trimethylammonium iodide O,O-diethyl phosphorothioate is 0.001%.

6. The method of claim 4, wherein the concentration of (2-mercaptoethyl) trimethylammonium iodide O,O-diethyl phosphorothioate is 0.0075%.

7. The method of claim 4, wherein the concentration of (2-mercaptoethyl) trimethylammonium iodide O,O-diethyl phosphorothioate is 0.015%.

8. The method of claim 4, wherein the concentration of (2-mercaptoethyl) trimethylammonium iodide O,O-diethyl phosphorothioate is 0.03%.

9. The method of claim 4, wherein the concentration of (2-mercaptoethyl) trimethylammonium iodide O,O-diethyl phosphorothioate is 0.12%.

10. The method of claim 4, wherein the concentration of (2-mercaptoethyl) trimethylammonium iodide O,O-diethyl phosphorothioate is 0.25%.

11. The method of claim 4, wherein the acetylcholine esterase inhibitor is contained in a pharmaceutically acceptable buffer solution.

12. A method for potentiating best visual acuity in a human which comprises topically administering to one or both eyes of the human an amount of a composition sufficient to inhibit acetylcholine esterase activity in the eye of the patient.

13. The method of claim 12, wherein the composition is administered at bedtime.

14. The method of claim 13, wherein said inhibitor is (2-mercaptoethyl) trimethylammonium iodide O,O-diethyl phosphorothioate.

15. The method of claim 14, wherein said (2-mercaptoethyl) trimethylammonium iodide O,O-diethyl phosphorothioate is present at a concentration of 0.001% to 0.25%.

16. The method of claim 15, wherein the concentration of (2-mercaptoethyl) trimethylammonium iodide O,O-diethyl phosphorothioate is 0.001%.

17. The method of claim 15, wherein the concentration of (2-mercaptoethyl) trimethylammonium iodide O,O-diethyl phosphorothioate is 0.0075%.

18. The method of claim 15, wherein the concentration of (2-mercaptoethyl) trimethylammonium iodide O,O-diethyl phosphorothioate is 0.015%.

19. The method of claim 15, wherein the concentration of (2-mercaptoethyl) trimethylammonium iodide O,O-diethyl phosphorothioate is 0.03%.

20. The method of claim 15, wherein the concentration of (2-mercaptoethyl) trimethylammonium iodide O,O-diethyl phosphorothioate is 0.012%.

21. The method of claim 15, wherein the concentration of (2-mercaptoethyl) trimethylammonium iodide O,O-diethyl phosphorothioate is 0.25%.

22. The method of claim 15, wherein the acetylcholine esterase inhibitor is contained in a pharmaceutically acceptable buffer solution.

23. A method of treating of a human patient suffering from Strabismus, the method comprising topically administering to both eyes of the human patient or to an eye affected with said Strabismus, an amount of (2-mercaptoethyl) trimethylammonium iodide O,O-diethyl phosphorothioate containing composition sufficient to provide a therapeutic benefit.

24. The method of claim 23, wherein the composition is administered at bedtime.

25. The method of claim 24, wherein said inhibitor is (2-mercaptoethyl) trimethylammonium iodide O,O-diethyl phosphorothioate.

26. The method of claim 25, wherein said (2-mercaptoethyl) trimethylammonium iodide O,O-diethyl phosphorothioate is present at a concentration of 0.001% to 0.25%.

27. The method of claim 26, wherein the concentration of (2-mercaptoethyl) trimethylammonium iodide O,O-diethyl phosphorothioate is 0.001%.

28. The method of claim 26, wherein the concentration of (2-mercaptoethyl) trimethylammonium iodide O,O-diethyl phosphorothioate is 0.0075%.

29. The method of claim 26, wherein the concentration of (2-mercaptoethyl) trimethylammonium iodide O,O-diethyl phosphorothioate is 0.015%.

30. The method of claim 26, wherein the concentration of (2-mercaptoethyl) trimethylammonium iodide O,O-diethyl phosphorothioate is 0.03%.

31. The method of claim 26, wherein the concentration of (2-mercaptoethyl) trimethylammonium iodide O,O-diethyl phosphorothioate is 0.12%.

32. The method of claim 26, wherein the concentration of (2-mercaptoethyl) trimethylammonium iodide O,O-diethyl phosphorothioate is 0.25%.

33. The method of claim 26, wherein the acetylcholine esterase inhibitor is contained in a pharmaceutically acceptable buffer solution.

34. A method of treating pupil dilation in a patient which comprises topically administering to both eyes of the human patient or to an eye affected with said pupil dilation, an amount of (2-mercaptoethyl) trimethylammonium iodide O,O-diethyl phosphorothioate containing composition sufficient to provide a therapeutic benefit.

35. The method of claim 34, wherein the composition is administered at bedtime.

36. The method of claim 35, wherein said inhibitor is (2-mercaptoethyl) trimethylammonium iodide O,O-diethyl phosphorothioate.

37. The method of claim 36, wherein said (2-mercaptoethyl) trimethylammonium iodide O,O-diethyl phosphorothioate is present at a concentration of 0.001% to 0.25%.

38. The method of claim 37, wherein the concentration of (2-mercaptoethyl) trimethylammonium iodide O,O-diethyl phosphorothioate is 0.001%.

39. The method of claim 37, wherein the concentration of (2-mercaptoethyl) trimethylammonium iodide O,O-diethyl phosphorothioate is 0.0075%.

40. The method of claim 37, wherein the concentration of (2-mercaptoethyl) trimethylammonium iodide O,O-diethyl phosphorothioate is 0.015%.

41. The method of claim 37, wherein the concentration of (2-mercaptoethyl) trimethylammonium iodide O,O-diethyl phosphorothioate is 0.03%.

42. The method of claim 37, wherein the concentration of (2-mercaptoethyl) trimethylammonium iodide O,O-diethyl phosphorothioate is 0.12%.

43. The method of claim 37, wherein the concentration of (2-mercaptoethyl) trimethylammonium iodide O,O-diethyl phosphorothioate is 0.25%.

44. The method of claim 37, wherein the acetylcholine esterase inhibitor is contained in a pharmaceutically acceptable buffer solution.

* * * * *